US012679864B2

(12) United States Patent
Chotteau et al.

(10) Patent No.: US 12,679,864 B2
(45) Date of Patent: Jul. 14, 2026

(54) PURIFICATION PROCESS BASED ON MAGNETIC BEADS

(71) Applicant: LAB-ON-A-BEAD AB, Uppsala (SE)

(72) Inventors: Veronique Chotteau, Nacka (SE);
Kristofer Eriksson, Strängnäs (SE);
Sven Oscarsson, Stockholm (SE); **Nils
Arnold Brechmann**, Stockholm (SE);
Per-Olov Eriksson, Strängnäs (SE)

(73) Assignee: LAB-ON-A-BEAD AB, Uppsala (SE)

( * ) Notice: Subject to any disclaimer, the term of this
patent is extended or adjusted under 35
U.S.C. 154(b) by 991 days.

(21) Appl. No.: 17/766,366

(22) PCT Filed: Oct. 5, 2020

(86) PCT No.: PCT/EP2020/077861
§ 371 (c)(1),
(2) Date: Apr. 4, 2022

(87) PCT Pub. No.: WO2021/064244
PCT Pub. Date: Apr. 8, 2021

(65) Prior Publication Data
US 2022/0389053 A1 Dec. 8, 2022

(51) Int. Cl.
*C12M 1/00* (2006.01)
*C07K 1/22* (2006.01)
(Continued)

(52) U.S. Cl.
CPC .............. *C07K 1/22* (2013.01); *C12M 29/10*
(2013.01); *C12M 47/10* (2013.01); *C12N
13/00* (2013.01); *C12P 21/02* (2013.01)

(58) Field of Classification Search
None
See application file for complete search history.

(56) References Cited

U.S. PATENT DOCUMENTS

2003/0166285 A1*  9/2003  Valerio ..................... A61P 7/00
435/456
2016/0184737 A1*  6/2016  Oscarsson .............. B01J 20/289
210/656
2021/0102153 A1*  4/2021  Griffin .................... B01F 31/23

FOREIGN PATENT DOCUMENTS

CN          102838674 A     12/2012
CN          104475041 A      4/2015
(Continued)

OTHER PUBLICATIONS

Chen et al., The GAGOme: a cell-based library of displayed
glycosaminoglycans, Aug. 13, 2018, Nature Methods, 15, 881-888
(Year: 2018).*

(Continued)

Primary Examiner — Holly Kipouros
(74) Attorney, Agent, or Firm — Branch Partners PLLC;
Bruce E. Black

(57) ABSTRACT
There is provided a process for the separation of molecules
from a suspension comprising cells at a concentration of at
least 56×10⁶ cells/ml, comprising the steps of: a) providing
magnetic particles having a specific interaction with said
molecules to be separated, b) mixing the magnetic particles
with the cell suspension containing the molecules, c) bring-
ing the cell suspension in contact with a magnetic field
provided by a magnetic separation device to collect the
magnetic particles, d) decreasing or removing said magnetic
field and collecting said magnetic particles carrying said
molecules, and e) removing said molecules from said mag-
netic particles, to provide a concentrated fraction of said
molecules, and/or provide partial or complete removal of
impurities and cells from the fraction containing the mol-
ecules. Advantages include that the yield increases, the
volume of the bioreactor and other equipment can be made
smaller so that the process becomes more economical.

21 Claims, 4 Drawing Sheets

(51) Int. Cl.
  *C12N 13/00*     (2006.01)
  *C12P 21/02*     (2006.01)

(56)          References Cited

FOREIGN PATENT DOCUMENTS

| WO | WO 2006041849 A2 | 4/2006 | |
| WO | 2015/034428 | 3/2015 | |
| WO | WO-2018098295 A1 * | 5/2018 | ........... C12M 25/14 |
| WO | 2018/122089 | 7/2018 | |
| WO | 2018/234115 | 12/2018 | |

OTHER PUBLICATIONS

Taninaka et al., Hidden variety of biotinastreptavidin/avidin local interactions revealed by site-selective dynamic force spectroscopy, 2010, Physical Chemistry Chemical Physics, Issue 39 (Year: 2010).*

Yeung et al., Quantitative Screening of Yeast Surface-Displayed Polypeptide Libraries by Magnetic Bead Capture, Biotechnol Prog. Mar.-Apr. 2002;18(2):212-20 (Year: 2002).*

Brechmann, N.A., Eriksson, P.-O., Eriksson, K., Oscarsson, S., Buijs, J., Shokri, A., Hjalm, G. and Chotteau, V. (2019), Pilot-scale process for magnetic bead purification of antibodies directly from non-clarified CHO cell culture. Biotechnol. Prog., 35: e2775. https://doi.org/10.1002/btpr.2775.

Moritz Ebeler, Ola Lind, Nils Norrman, Ronnie Palmgren, Matthias Franzreb, One-step integrated clarification and purification of a monoclonal antibody using Protein A Mag Sepharose beads and a cGMP-compliant high-gradient magnetic separator, New Biotechnology, vol. 42, 2018, pp. 48-55.

Singh et al., "Clarification of recombinant proteins from high cell density mammalian cell culture systems using new Improved depth filters", Biotechnology and bioengineering, (20130000), vol. 110, No. 7, pp. 1964-1972.

Tomic et al., "Complete clarification solution for processing high density cell culture harvests", Separation and Purification Technology, (20150000), vol. 141, doi:10.1016/j.seppur.2014.12.002, pp. 269-275, XP029132484.

Clincke et al., "Very high density of CHO cells in perfusion by ATF or TFF in WAVE bioreactor™. Part I. Effect of the cell density on the process", Biotechnology progress, (20130000), vol. 29, No. 3, pp. 754-767.

Clincke et al., "Very high density of Chinese hamster ovary cells in perfusion by alternating tangential flow or tangential flow filtration in WAVE bioreactor™—part II: Applications for antibody production and cryopreservation", Biotechnology progress, (20130000), vol. 29, No. 3, doi:10.1002/btpr.1703, pp. 768-777, XP055168922.

International Search Report and Written Opinion for PCT Application No. PCT/EP2020/077861 mailed Mar. 4, 2021.

International Preliminary Report on Patentability for PCT Application No. PCT/EP2020/077861 mailed Apr. 5, 2022.

Ebeler M. et al., 'Separation on a New Level: Characterization and Performance Prediction of a cGMP Compliant "Rotor-Stator" High-Gradient Magnetic Separator', Biotechnol J, 2018, vol. 13, e1700448, pp. 1-6.

Chotteau V. et al "Very High Cell Density in Perfusion of CHO cells by ATF. TFF. Wave bioreactor and/or cellTank Technologies—Impact of Cell Density and Applications" In: Continuous processing in pharmaceutical manufacturing, Subramanian, G.: John Wiley & Sons, 2014, pp. 339-354, ISBN 9783527673711, see pp. 347-349; p. 349, paragraph (0002).

* cited by examiner

Adsorption curve

Binding and Elution percentage

PURIFICATION PROCESS BASED ON MAGNETIC BEADS

CROSS-REFERENCE TO RELATED APPLICATIONS

This present application is a U.S. national stage application of PCT Application No. PCT/EP2020/077861, filed Oct. 5, 2020, which claims priority to Swedish Patent Application No. 1930317-1 filed Oct. 5, 2019, both of which are hereby incorporated by reference in their entirety.

TECHNICAL FIELD

The present invention relates to a method for extraction from a dense cell broth.

BACKGROUND OF THE INVENTION

Large molecules and assemblies such as polypetides, proteins, enzymes, viral vectors, viruses, polysaccharides, polymers, exosomes, mRNA, siRNA, are usually produced using cells due to their complex and/or large structure. These molecules or assemblies are used for various aims, such as therapies for humans or animals, diagnostics, support for analytical methods, support for the biomanufacturing using cells, food, etc. In the rest of the text, large molecules and assemblies are designated by the generic name of 'large molecules' for simplicity but it is understood that 'large molecules' include as well assemblies. For the area of human and animal therapies, examples of these molecules are antibodies, enzymes, polysaccharides, polymers, polypeptides and any combinations of these. Another example is the production of viruses or viral particles, which can also be combined to polypeptides or polymers. These are, for instance, used for the production of vaccines, for gene therapy or for cell therapy when the gene has been modified. For the production of these large molecules, living cells or tissue are often used. In case of cell-based production, this is typically carried out in a container, such as a bioreactor, in which the cells are cultured in a suitable liquid, so called medium, which provides the nutrients and other necessary factors to the cells. Alternatively tissues from living organisms, animal or plant, where the production of the larges molecules is taking place, are used.

When large molecules are to be harvested from cultures, a challenge is the extraction or separation of the large molecules from the cells, the cell debris or other molecules generated by the cells during the culture. In the case where the cells are superior eukaryotes, so called animal cells such as mammalian cells, human cells, bird cells or insect cells, potentially the large molecules are outside of the cells, after the cells have secreted them in the culture medium. This can also be the case for microorganisms, such as bacteria or fungi. Alternatively, the cells of superior eukaryotes or the tissue or the microorganisms have to be disrupted to release the large molecules before these can be separated from the cell debris, the other molecules produced by the cells or potentially some cells, which have not been disrupted.

According to the state-of-the-art technology, in the case of processes based on animal cells for the production of large molecules, at harvest of the culture, the cells are first removed in a clarification step, generating the cell-free supernatant. The cell-free supernatant contains the large molecules (which are the product of interest), and impurities. These impurities are cell debris, DNA from the cells, and many other molecules, which have been generated by the cells or which were present in the culture medium. The cell-free supernatant is then further processed through a series of purification steps. The purpose of the first of these purification steps is to provide a volume reduction and a purification in which impurities are eliminated. The subsequent purification steps are then further removing impurities and improving the purity of the large molecules while further reducing the volume. The first purification step, often denoted as capture step, is typically based on the interaction of the large molecules with a solid support, where the interaction can be for instance affinity for a given molecule, affinity for an ion exchanger, hydrophilic interaction, etc. and the solid support can be for instance beads of resin, membrane, matrix, etc. The clarification step, also called cell separation step, is performed by filtration in filter unit(s) or by centrifugation in a centrifuge. New technologies associating flocculation and filtration are also available. These provide separations up to a cell concentration of $30\times10^6$ cells/ml [Singh, Nripen, et al. "Clarification of recombinant proteins from high cell density mammalian cell culture systems using new improved depth filters." Biotechnology and bioengineering 110.7 (2013): 1964-1972; Tomic, Sladjana, et al. "Complete clarification solution for processing high density cell culture harvests." Separation and Purification Technology 141 (2015): 269-275].

In order to increase the efficiency of the processes producing these larges molecules, the concentration of the cells can be selected to be very high with the principle that a high cell concentration in the bioreactor, gives a high amount of produced large molecules. The cell density can be increased to very high levels when the culture medium is renewed since this provides enough nutrients to the cells and also eliminates the toxic by-products from the culture.

The medium renewal can be operated in so called perfusion mode. In perfusion mode, the medium of the culture is continuously or semi-continuously renewed. For this a cell retention device (such as a system based on hollow fibre tangential flow filtration operated in one direction or in alternating direction, a centrifuge, an inclined settler, a hydrocyclone) ensures that the cells are retained in the bioreactor while the culture medium free of cell is automatically removed. As the medium free of cells is removed from the bioreactor, fresh medium is continuously added to the bioreactor so that the culture volume stays constant. Using this type of operation, cell concentrations higher than $200\times10^6$ cells/ml have been reported [Clincke, Marie-Francoise, et al. "Very high density of CHO cells in perfusion by ATF or TFF in WAVE bioreactor™. Part I. Effect of the cell density on the process." Biotechnology progress 29.3 (2013): 754-767]. In some applications, it is desirable that the cell density remains constant although the cells have a natural tendency to continue to grow. In that case, partial cell removal, so called cell bleed, can be performed so that the cell density remains constant. The partial cell removal (or cell bleed) is often discarded, and can represent a substantial loss of the product of interest. In some cases, the cell retention device is a tangential flow filtration system equipped with an ultra-filter hollow fibre allowing the passage of only very small molecules, e.g. allowing the passage only of molecules smaller than 50 kDa. This allows small molecules, which can potentially be toxic for the cells, to be removed from the culture while large molecules, in particular the product of interest, are retained in the bioreactor. Using this type of operation, cell concentrations higher than $100\times10^6$ cells/ml have been reported [Clincke, Marie-Francoise, et al. "Very high density of Chinese hamster ovary cells in perfusion by alternating tangential flow or tangential flow filtration in WAVE bioreactor™-part II: Applications for antibody production and cryopreservation." Biotechnology progress 29.3 (2013): 768-777]. An advantage is that only one harvest needs to be operated since the product of interest has been accumulated in the bioreactor. Finally, some processes use the perfusion mode only for a short period of time to substantially increase the cell density, after which the perfusion is discontinued, generating a harvest with a very high cell density, i.e. larger than $40 \times 10^6$ cells/ml.

This type of intensification has however the drawback that very high cell densities are very challenging for the cell separation step. A practice in the field is, in this case, to dilute the culture to be harvested with an osmotic salt solution before the cell clarification step. Unfortunately, this increases the volume of the cell-free supernatant enormously and counteracts one of the purification purposes, which is to reduce the liquid volume.

Furthermore, when the cell density is very high, for instance larger than $50 \times 10^6$ cells/ml or larger than $80 \times 10^6$ cells/ml, the culture includes as well a very large amount of cell debris and DNA, which are released when some of the cells die in the culture and typically accumulate with time in the culture. These cell debris and DNA are known to be unfavorable for filtration operations.

The potential advantages of a method using very high cell densities including for instance high yield, high concentration of the end product, and a smaller reactor cannot be fully utilized because of the problems with extraction of large molecules from medium comprising a high cell density with about $56 \times 10^6$ cells/ml or larger.

WO 2018/234115 discloses separation with magnetic beads having a specific affinity for molecules and a magnetic field to attract the beads loaded with molecules of interest. The magnetic beads can be attracted in a magnetic field and subsequently eluted. The method can be used for cells.

Brechmann N. A et al., in, Biotechnol Prog, 2019, Vol. 35, e2775, pages 1-10 discloses growth of CHO cells which at the harvest had a total cell density of $14 \times 10^6$ cells/ml. In a second experiment the cell density at harvest was $11.2 \times 10^6$ cells/ml. High capacity magnetic protein A agarose beads were utilized for affinity purification of monoclonal antibodies (mAbs) from non-clarified CHO cell broth. For smaller samples the cell concentration was increased by adding cells concentrated by centrifugation to the sample after the harvest. This allowed achieving cell concentrations $20 \times 10^6$ and $40 \times 10^6$ cells/ml as well as more dilute cell concentrations $1 \times 10^6$ and $10 \times 10^6$ cells/ml. The centrifugation step provided concentrated cells free from dead cells, and impurities such as DNA and cell debris. On the contrary, a cell culture, which is pushed to higher cell concentration by cell growth in a bioreactor includes large amount of cell debris and DNA, which are typically released when some of the cells die in a culture with very high cell density. Thus, this assay in this document is not a perfectly realistic assay for high cell densities with regard to cell debris and DNA. The bead capacity usage was only about 50% for the example with a cell density of $40 \times 10^6$ cells/ml. This does not give a good answer whether the method is suitable in an industrial application at that cell concentration, since 50% bead capacity usage is more likely to work since there is a large surplus of beads, e.g. 2 times the amount of beads necessary to bind the molecules. Therefore, it is not certain that such a setup would be efficient for more realistic bead capacity usage such as 85-99%, e.g. the amount of beads necessary to bind the molecules.

SUMMARY OF THE INVENTION

It is an object of the invention to alleviate at least some of the problems in the prior art and provide an improved system for extraction of molecules from a dense cell suspension.

The present invention surprisingly provides in a one-step operation a way to separate the large molecules from the cells (i.e. cell clarification) and perform a capture step (i.e. a first purification in which impurities are removed and the harvest volume is reduced) to harvest cell suspension of concentrations larger than $56 \times 10^6$ cells/ml, or larger than $80 \times 10^6$ cells/ml. The culture can have a working volume larger than 100 ml. For this, magnetic beads with a given affinity property are used, where the affinity property is used to capture the large molecules in the cell suspension. The present one step operation consists in adding these magnetic beads directly to the cell suspension at harvest, rinsing off the cells, cell debris, and other impurities, collecting the beads, and extracting the large molecules from the beads, i.e. performing an elution.

Furthermore, despite the very high concentration of the cells and the presence of magnetic beads, the cells are not dramatically damaged. This represents an advantage compared to the state-of-the art cell clarification technology by centrifugation or filtration, where the cells are damaged or disrupted during the cell separation step causing the cell content to be released in the cell-free supernatant and thus increasing the level of impurities in this supernatant.

In Brechmann et al 2019 [Brechmann, Nils A., et al. "Pilot-scale process for magnetic bead purification of antibodies directly from non-clarified CHO cell culture." Biotechnology progress (2019)], a process up to a cell density of $16 \times 106$ cells/ml was harvested using magnetic beads. However, in this case, the cells were not at a very high concentration and could have been clarified by centrifugation or by filtration, for instance by tangential flow filtration. On the contrary, when the cell concentration is very high such as larger than $56 \times 10^6$ cells/ml, filtration or centrifugation are not efficient as mentioned above.

Here the volume of the culture is also an important impediment. Magnetic beads are currently used in the field for analytical purpose in the range of microliters to several milliliters however, volumes of cell suspension larger than 100 ml are challenging due the need of very strong magnetic attraction, and have never been reported for cell densities larger than $16 \times 10^6$ cells/ml for the purification of large molecules.

BRIEF DESCRIPTION OF THE DRAWINGS

The invention is described with reference to the following drawings in which.

DETAILED DESCRIPTION OF THE INVENTION

Figure 1A:
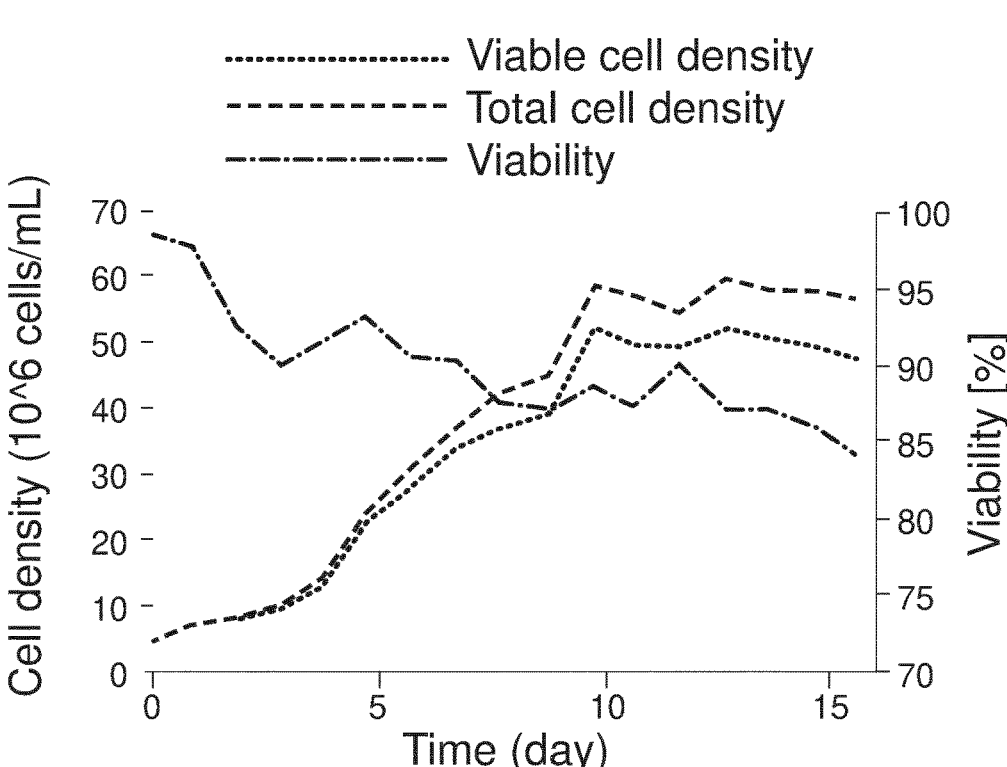
FIG. 1a shows cell density and viability in 200 ml bioreactor run in perfusion mode.

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "perfusion" as used throughout the description and the claims refers to a method for growing cells in a cell culture inside a bioreactor while continuously removing cell waste products and media depleted of nutrients by cell metabolism. Fresh media is provided to the cells at the same rate as the spent media is removed. One example of a means to achieve perfusion is the use of hollow fiber filtration.

Perfusion generally saves time and allows to reduce bioreactor size in the seed train, while production perfusion processing gives much higher protein yields than fed batch. One of the key advantages with perfusion is its flexibility— the technology is compatible with small, portable plants, and can be used with many drug types over a range of production scales. Also, often perfusion is used with hybrid systems; for example, the combination of fed-batch and perfusion processing. Generally, the term "production perfusion" is interpreted as a process in which the cells are maintained in a steady state, most commonly by active cell bleeding. However, an alternative modality quite commonly used implements a dynamic perfusion in which the cell density is not restrained and viability is allowed to drop similarly to a fed-batch process. Modalities used in the industry for perfusion protein production include microfiltration (or equivalent perfusion systems in which protein is being collected in the harvest), ultrafiltration or hybrid perfusion/fedbatch processes, some times reported at 'intensified fedbatch'. Typically some filters, such as ultrafilter, can allow the retention of a certain category of components in a perfusion process, like for instance all the molecules larger than a given cut off are retained in the bioreactor while the molecules smaller than this cut off are removed from the culture.

All ratios and percentages are calculated by weight unless otherwise clearly indicated.

In a first aspect there is provided a process for the separation of molecules from a suspension comprising cells at a concentration of at least $56\times10^6$ cells/ml, comprising the steps of:

providing magnetic particles having a specific interaction with said molecules to be separated;

mixing the magnetic particles with the cell suspension containing the molecules;

bringing the cell suspension in contact with a magnetic field provided by a magnetic separation device to collect the magnetic particles;

decreasing or removing said magnetic field and collecting said magnetic particles carrying said molecules;

removing said molecules from said magnetic particles, to provide a concentrated fraction of said molecules, and/or provide partial or complete removal of impurities and cells from the fraction containing the molecules.

A cell suspension with high concentration (above $56\times10^6$ cells/ml) is provided and mixed with the magnetic particles. The magnetic particles have an affinity for the molecules to be extracted from the cell suspension. Typically the "specific interaction" means that there is a specific net attraction so that only the desired type of molecules are bound. The molecules of interest at least partially bind to the magnetic particles by the specific interaction.

Unspecific binding is generally low because of the specificity in the interaction. The magnetic particles are collected with a magnetic field, such as an electromagnet and/or a permanent magnet. After collection the magnetic particles are optionally washed and then the bound molecules are eluted by changing the conditions such as for instance pH, ionic strength and temperatures etc so that the specific affinity decreases or even becomes a repulsion. This releases the molecules and gives a concentrated fraction comprising the molecules of interest.

The steps are intended to be performed sequentially.

In one embodiment, the process comprises an initial step of growing cells in a cell medium in a bioreactor, wherein a perfusion method is used, wherein spent cell medium depleted of nutrients and including cell waste products is removed and wherein fresh cell medium is provided to the cells in the bioreactor at the same rate as spent media is removed, wherein molecules with a molecular weight over a determined cut off value are not removed together with the spent cell medium, and wherein the cells in the cell medium form the suspension comprising cells, which suspension is used in the subsequent step without any filtration.

In one embodiment, there is no dilution step before the magnetic beads are added.

The step with growth of cells in a perfusion reactor precedes the purifications step. In one embodiment, the perfusion reactor is connected in series before the equipment for the purification with the magnetic beads.

By the combination of a perfusion reactor and subsequent purification with magnetic beads a number of advantages can be achieved. The yield increases, the volume of the bioreactor and other equipment decreases, the product molecules becomes highly concentrated in the cell suspension, which gives higher reaction speed for the binding to the particles. No mechanical filtration is necessary and this is also not even suitable because of the high cell concentration. It is also not necessary to dilute the cell suspension from the reactor, such a dilution would make the process less economical and less efficient because of the lower concentration of molecules. Perfusion bioreactors can be used with their advantages, and the desired molecules can be recovered easier without dilution, without difficult filtration or other difficult cell separation by centrifugation when combined with purification with magnetic particles.

The lower volumes give a more economical process for instance since smaller reactors and equipment with lower volume can be used for the same amount of manufactured molecules.

The perfusion process is potentially operated with a certain cut off value for the size of the molecules to be removed. The molecules with a molecular weight over a determined cut off value are not removed together with the spent cell medium. In one embodiment, the cut off value is 50 kD. The cut off value can be adjusted depending on the molecules to be extracted and the type of cell culture as well as other factors.

In one embodiment, the bead capacity usage is at least 60%, preferably at least 70%, more preferably at least 80%, even more preferably at least 85%, and most preferably at least 90%. In one embodiment, the bead capacity usage is at least 95%. A higher bead capacity usage gives better economy since less magnetic particles have to be added. It is preferred to have a high capacity usage of the magnetic beads. The DBBC is defined as the amount of magnetic beads that has the ability to bind 90 wt % of the molecules of interest in a mixture of molecules with a defined concentration of the molecules of interest after 1 hour of contact time. The DBBC typically varies with the concentration of molecules of interest in the solution. The bead capacity usage is defined as the amount of molecules of interest in the mixture divided by the DBBC (i.e. the amount of magnetic beads that can bind 90 wt % of the molecules of interest).

In one embodiment, the magnetic particles and the cell suspension containing the molecules are in contact no more than 45 minutes after the mixing. In a setting with a perfusion reactor the concentration of the molecules to be extracted are generally high and thus the reaction where the molecules are bound to the particles is very fast and faster than the corresponding setup where the cell density is lower with a corresponding lower concentration of molecules. It is an advantage that the contact time between the magnetic beads and the suspension of cells is short since the process can be made shorter and more economical. In one embodiment, the magnetic particles and the cell suspension containing the molecules are in contact no more than 40 minutes after the mixing. In one embodiment, the magnetic particles and the cell suspension containing the molecules are in contact no more than 30 minutes after the mixing. In one embodiment, the magnetic particles and the cell suspension containing the molecules are in contact no more than 10 minutes after the mixing. In one embodiment, the magnetic particles and the cell suspension containing the molecules are in contact no more than 5 minutes after the mixing. An additional advantage of keeping the contact time low is that the degree of unspecific binding decreases. Compared to the prior art this invention is able to achieve shorter contact times and thereby less unspecific binding.

In one embodiment, the suspension comprising cells has a concentration of at least $70 \times 10^6$ cells/ml. This refers to the cell concentration in the suspension when the magnetic particles are added to the suspension. In one embodiment, the suspension comprising cells has a concentration of at least $80 \times 10^6$ cells/ml. In one embodiment, the suspension comprising cells has a concentration of at least $90 \times 10^6$ cells/ml. In one embodiment, the suspension comprising cells has a concentration of at least $100 \times 10^6$ cells/ml.

The cells in the suspension occupy a certain fraction of the total volume of the cell suspension. In one embodiment, the suspension comprising cells is such that the volume of the cells occupies at least 12% of the culture volume, and the cell suspension is any one from the group consisting of cell culture, microorganism fermentation and cell suspension derived from cell tissue. In one embodiment, the cells occupies at least 12% of the volume of the cell suspension. In one embodiment, the cells occupies at least 15% of the volume of the cell suspension. In one embodiment, the cells occupies at least 20% of the volume of the cell suspension. In one embodiment, the cells occupies at least 25% of the volume of the cell suspension. In one embodiment, the cells occupies at least 30% of the volume of the cell suspension. This percentage is calculated by volume and not by weight.

The conversion factor between cell density measured as the number of cells per ml and the volume occupied by the cells of the total volume of the cell suspension depends on the volume of each of the cells. If all the cells can be assumed to be spheres and have essentially the same size, then the cell diameter can be used to calculate the volume occupied by the cells. A non-limiting example of a cell diameter is 17-19 μm.

In one embodiment, the magnetic particles comprise a component selected from the group consisting of agarose, silica, cellulose, polyvinyl alcohol, polyethylene glycol, polystyrene, acrylate, dextran, and derivatives thereof.

In one embodiment, the magnetic particles comprise at least one functional group selected from the group consisting of —SH, —SS-pyridine, —COOH, —NH2, —CHO, —OH, phenol, anhydride, epoxy an S—Au, an amide, an aminoethyl group, a diethylaminoethyl group, a quaternary ammonium group, a carboxymethyl group, a phosphate group, and a sulfopropyl group.

In one embodiment, the magnetic particles comprise at least one entity selected from the group consisting of IDA (iminodiacetic acid) and derivatives thereof, TED (tris(carboxymethyl)ethylenediamine) and derivatives thereof, CM-Asp (carboxymethylated aspartic acid) and its derivatives, NTA (nitrilotriacetic acid) and its derivatives, TREN (tris (2-aminoethyl)amine) and its derivatives, In one embodiment, the magnetic particles comprise at least one functional group selected from the group consisting of DPA (lutidine) and its derivatives, C6-S gel (hexylthio group) and its derivatives, EDTA (ethylenediaminetetraacetic acid) and its derivatives.

In one embodiment, the magnetic particles carry at least one selected from the group consisting of $C_nH_m$ ($1 \leq n \leq 20$, $4 \leq m \leq 42$), phenol and its derivatives, thiophenol and a group of derivatives and a group consisting of mercaptopyridine and its derivatives.

In one embodiment, the magnetic particles comprise at least one functional group comprising at least one group which is produced by reaction with at least one compound selected from the group consisting of divinyl sulfone, benzene anthracene, imidazole, periodate, trichloro-S-triazine, toluenesulfonate, diazo compound, isourea salt, carbodiimide, hydrazine, epichlorohydrin, glutaraldehyde, cyanogen bromide, double ethylene oxide, carbonyl diimidazole, N-hydroxysuccinimide, silane, and derivatives thereof.

In one embodiment, the affinity is obtained using molecules suitable for molecular interaction introduced on magnetic particles. In one embodiment, the molecule suitable for molecular interaction is at least one selected from the group consisting of organic molecules, proteins, antigens, enzymes, enzyme inhibitors, cofactors, hormones, toxins, vitamins, glycoconjugates, nucleic acids, antibodies, peptides, lectins, and carbohydrates. In one embodiment, the molecules for molecular interaction (i.e. affinity) attached to the particles is protein A. The molecule suitable for molecular interaction is one that gives a specific net attraction so that it can bind the desired molecule specifically.

In one embodiment, the magnetic particles comprise particles of at least one magnetic material embedded in a polymer matrix, and wherein the polymer matrix comprises functional groups.

In one embodiment, the cell suspension containing the molecules comprises at least one selected from the group consisting of alive cells, dead cells, ruptured cells, lysed cells, cell debris, cell membrane, proteins, peptides, DNA, RNA, ions, amino acids, organic compounds, salts, water, solvents and/or metals. In one embodiment, the cells are eukaryotic cells. In one embodiment, the eukaryotic cells are selected from the group consisting of mammalian cells, human cells, avian cells, insect cells and plant cells. In one embodiment, the cells are selected from the group consisting of: CHO, CHO-DBX11, CHO-DG44, CHO-S, CHO-K1, Vero, BHK, HeLa, COS, MDCK, HEK-293, HEK-293T, HEK-293S, HEK-293F, L293, NIH-3T3, W138, BT483, Hs578T, HTB2, BT20, T47D, NSO, CRL7030, HsS78Bst cells, PER.C6, SP2, SP0, hybridoma, MRC-5, MDCK, WI-98, CAP, EB66, AGE1.CR, CR, Trichoplusia ni, Spodoptera Frugiperda, SF9, SF21, Hi5, mesenchymal stem cells, induced pluripotent stem cells, embryonic stem cells, primary cells, Nicotiana tabacum, BY2, Nicotiana benthamiana, Oriza sativa, Arabidopis thaliana, and Daucus carota. In one embodiment, the cells are CHO cells.

In one embodiment, the molecules are polypetides, proteins, antibodies, enzymes, viral vectors, viruses, polysaccharides, polymers, exosomes, mRNA, siRNA, or any combination of these, or assemblies derived from these, or assemblies derived from these and associated with a small molecule of a size less than 1000 kDa.

In one embodiment, the cells are selected from the group consisting of *Escherichia coli*, yeast, Saccharomyces cerevisiae, Pichia pastoris, and Aspergillus niger.

In one embodiment, the cells are ruptured or lysed by mechanical disruption, ultrasonication, osmotic shock, freeze-thaw, pressure homogenisation, heat treatment or chemical action such as, but not limited to, the addition of detergent or solvent disrupting the cell membrane. In one embodiment, this is made before the cells are contacted with the magnetic particles. In an alternative embodiment this is made after the cells are contacted with the magnetic particles. Combinations of these alternatives are also encompassed.

In one embodiment said magnetic particles are washed at least once before removing said molecules from said magnetic particles. The washing is in one embodiment performed directly after the collection of the magnetic beads.

In a second aspect there is provided a system for production of molecules comprising:
a. a perfusion bioreactor suitable for growing cells expressing the molecules to a cell density higher than $56 \times 10^6$ cells/ml, the perfusion bioreactor having at least one inlet and at least one outlet,
b. at least one magnet positioned to exert a magnetic field to at least a part of a compartment, wherein the perfusion bioreactor is connected in series to the compartment, and
c. magnetic beads having a specific affinity for the molecules.

In one embodiment, the bioreactor is adapted to accommodate at least 100 ml cell suspension.

In one embodiment, the perfusion bioreactor and the compartment are connected in series.

EXAMPLES

Example 1

In Example 1, a culture of Chinese Hamster Ovary (CHO) cells producing an antibody was performed in a bioreactor of 200 ml working volume where the cells were grown in suspension. This cell line expressed the antibody since the gene of this antibody has been inserted in the cells by recombinant technology. The purpose of this culture was to produce this antibody, which is thus the product of interest.

Figure 1B:
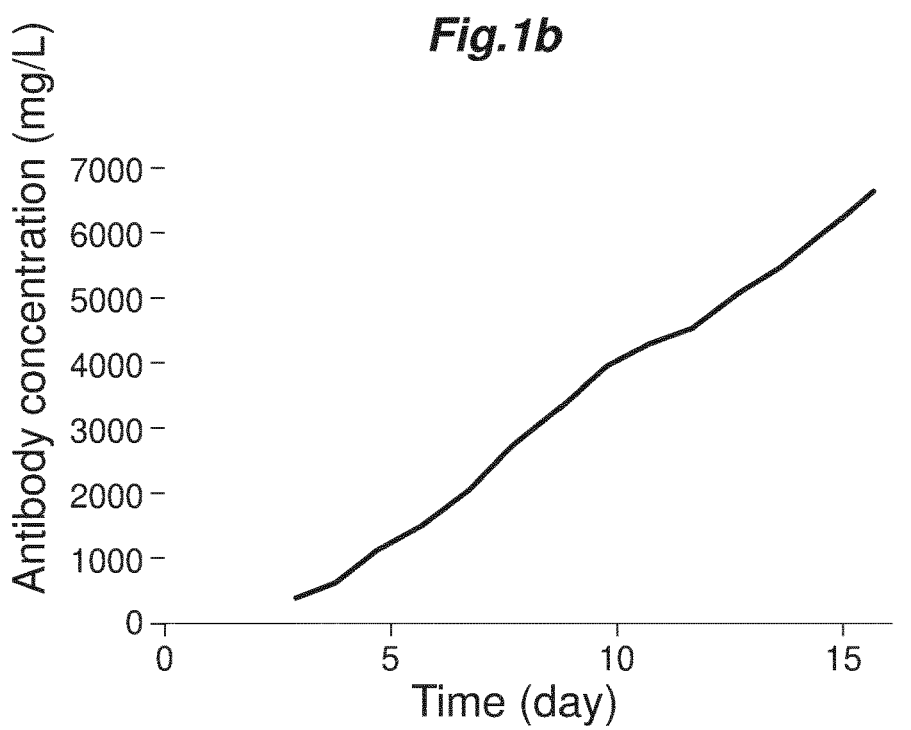
FIG. 1b shows accumulation of antibody in the bioreactor ending at a concentration of 6600 mg/l
Figure 2A:
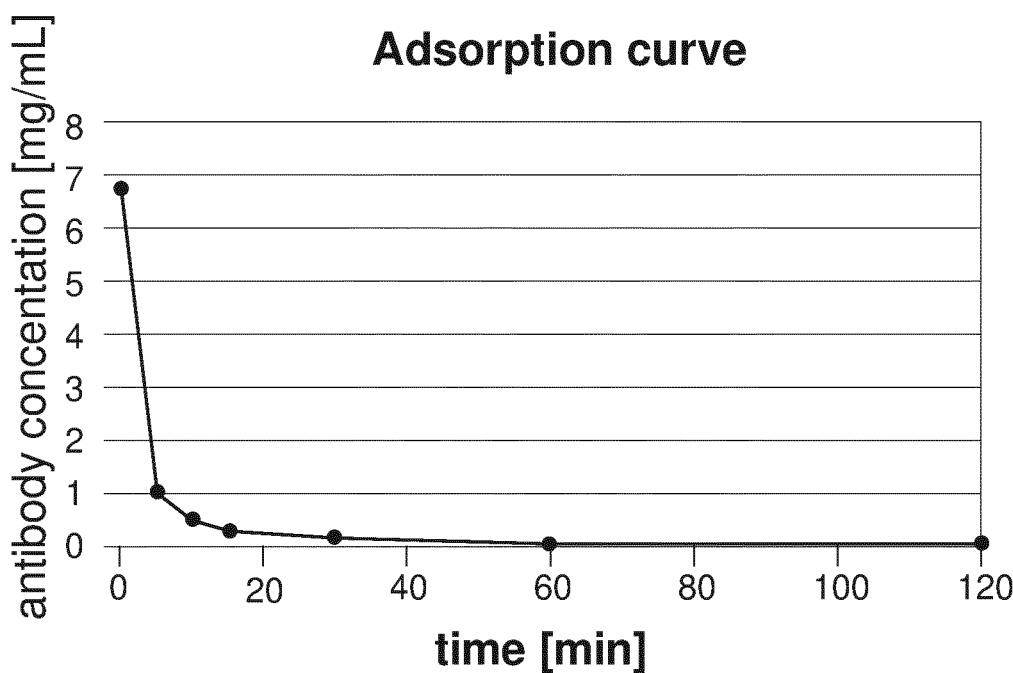
FIG. 2a shows adsorption of the antibody in the mixture of the magnetic beads and the cell suspension of the bioreactor. The concentration of the antibody is given as a function of time in minutes, where 0 is the time of addition of the magnetic beads to the cell suspension. The concentration of antibody decreases with time since the antibody molecules are adsorbed on the magnetic beads and are not detected anymore in the cell suspension.
Figure 2B:
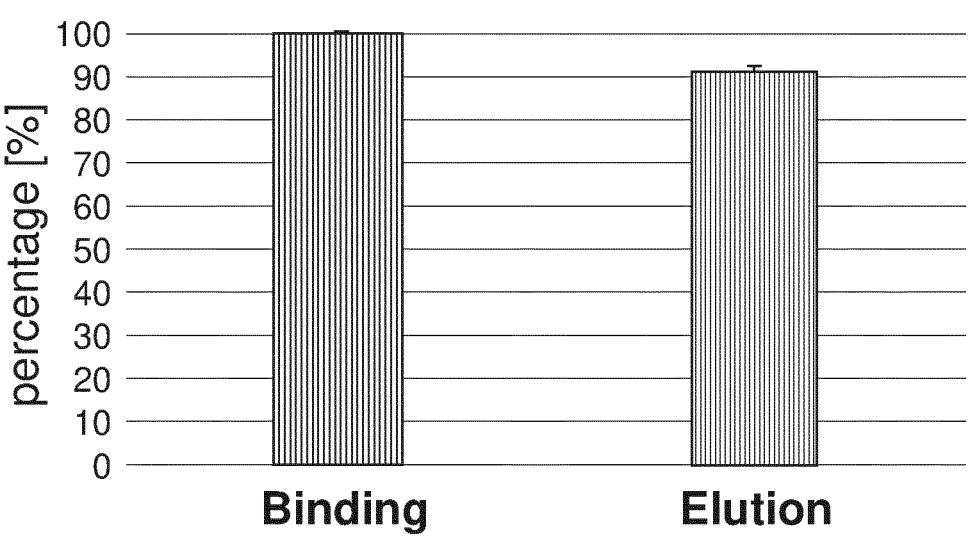
FIG. 2b shows yields of the binding step after two hours of adsorption and yield of the elution step. As can be seen there is complete adsorption already after 20 minutes, so in this particular case an adsorption time of more than 20 would not be necessary.

To initiate the culture, the bioreactor was filled with culture medium. This medium contained the components necessary for the cells to grow and produce antibody, including sugar, amino acids, vitamins, salts, buffer, metal traces, organic components. The cells were inoculated at day 0 from a stock culture maintained in shake flasks. The bioreactor was equipped with a cell retention system Alternative Tangential Flow Filtration with an ultra-filter of 50 kDa cut-off. This allowed performing perfusion operation. With this ultra-filter, the small molecules, which can potentially be toxic for the cells, were removed from the culture while large molecules, in particular the antibody molecules, were retained in the bioreactor. The culture medium was continuously removed from the culture while fresh medium was automatically added so that the culture level was maintained. At day 16, the culture was stopped, the cell density was $56.8 \times 10^6$ cells/ml (see FIG. 1a) and the cell viability, defined as the ratio between the viable cells and the total cell density, was 84% (see FIG. 1a). The cells had produced antibodies, which had accumulated in the cell suspension of the bioreactor up to a concentration of 6.6 g/l (see FIG. 1b). The purification was started with the cell suspension of the bioreactor immediately after the termination of the culture by the adsorption of the antibody molecules on the magnetic beads. For this, a volume of 35 ml protein A coupled magnetic beads, which have the property to bind the antibody, was added to 200 ml cell suspension. The adsorption phase was performed during at least 5 minutes. FIG. 2a shows the adsorption of the antibody in the mixture of the magnetic beads and the cell suspension of the bioreactor. The concentration of the antibody is given as a function of time in minutes, where 0 is the time of addition of the magnetic beads to the cell suspension. The concentration of antibody decreases with time since the antibody molecules, which are adsorbed on the magnetic beads, are not detected anymore in the cell suspension. For this experiment, the adsorption has been performed during two hours to study the kinetics of adsorption of the antibody molecules on the magnetic beads, however one can see that a shorter time than 2 hours is sufficient to capture the antibody on the magnetic beads. For instance, a time of 5 minutes gives already a substantial capture of the antibodies on the beads and after 10 minutes of adsorption, the residual concentration of antibody in the sample is 0.5 g/l. It is an advantage that such short adsorption times can be used. The next step was a washing step with phosphate buffer to remove the cells, cell debris and other impurities. After this, an elution with 35 ml citrate buffer at low pH was performed twice to recover the antibody molecules from the magnetic beads. The low pH elution step was also a step providing virus reduction. FIG. 2b shows the yield of the elution, where it can be seen that more than 90% of the antibody molecules present in the cell suspension of the bioreactor are recovered. From the 1.32 gram antibody present in the 200 ml cell suspension, 1.20 gram antibody was finally recovered in a volume of 70 ml buffer, representing a volume reduction by a factor 2.9. Analyzing the purity of the eluted monoclonal antibody regarding the contamination of host cell proteins (HCP), a final HCP concentration in the eluate was found to be 3.4 ppm resulting in a logarithmic reduction factor (LRV) of 2.3. After this, the beads can be re-used in multiple new cycles of purification after a washing procedure with citrate buffer, with PBS and with NaOH.

Example 2

In Example 2, a culture of Chinese Hamster Ovary (CHO) cells producing an antibody was performed in a bioreactor of 200 ml working volume where the cells were grown in suspension. This cell line expressed the antibody since the gene of this antibody had been inserted in the cells by recombinant technology. The purpose of this culture was to produce this antibody, which is thus the product of interest.

Figure 3A:
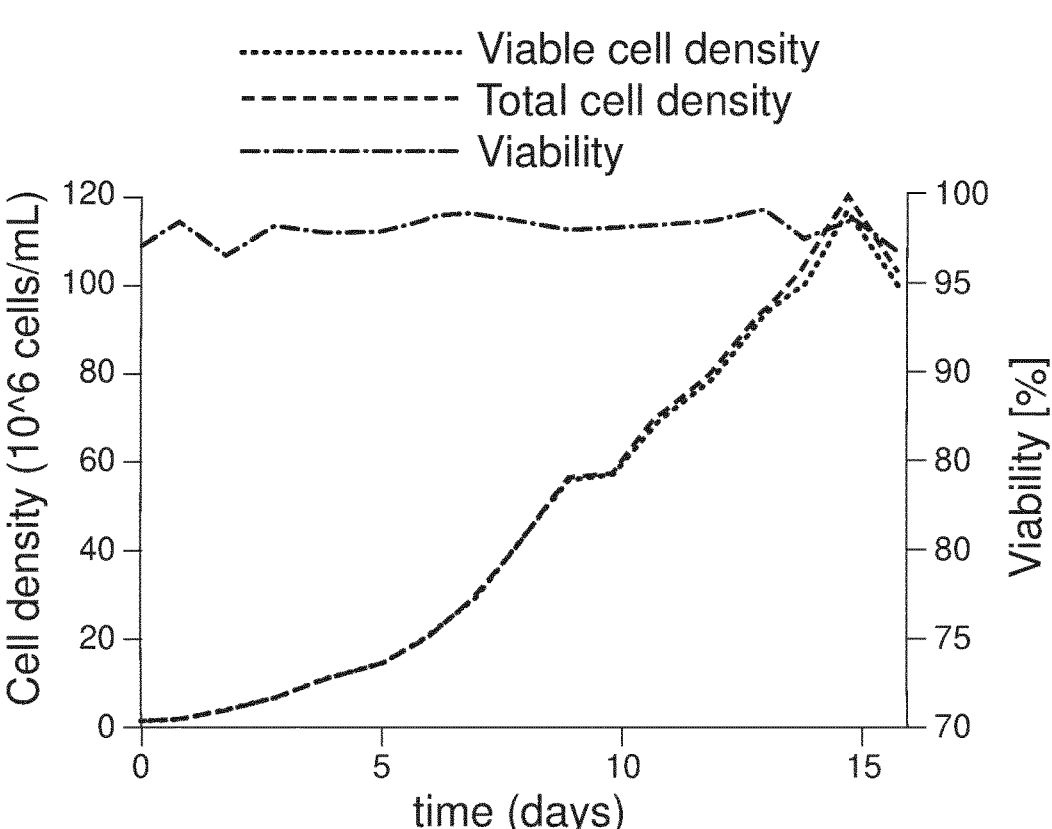
FIGS. 3a and 3b show the corresponding data as in FIGS. 1a and 1b, but for example 2 instead of example 1.
Figure 3B:
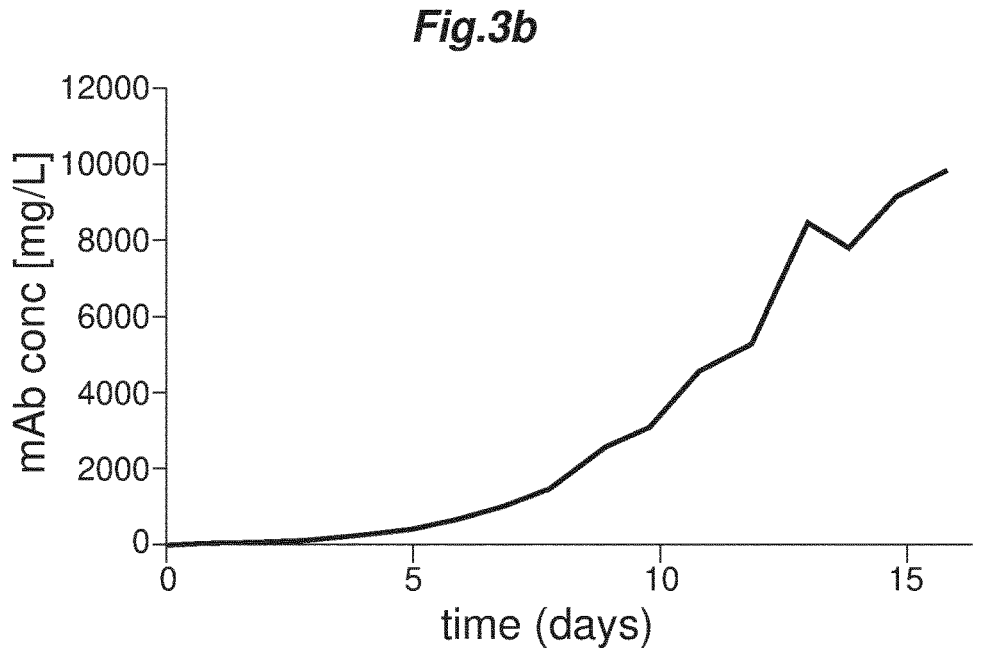
Figure 4A:
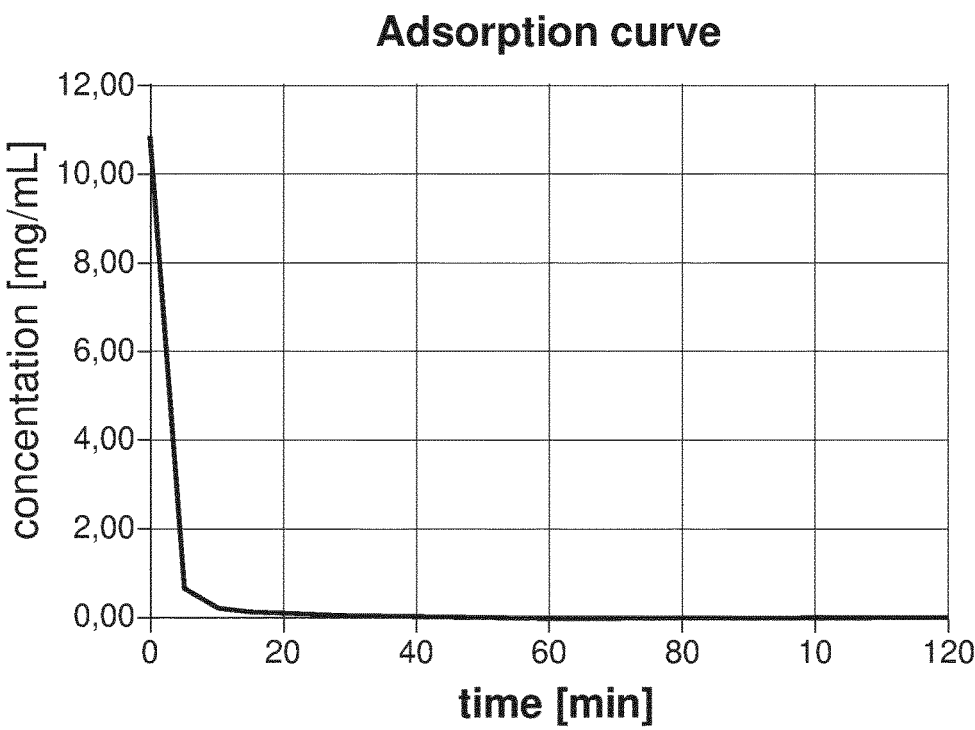
FIGS. 4a and 4b show the corresponding data as in FIGS. 2a and 2b, but for example 2 instead of example 1.
Figure 4B:
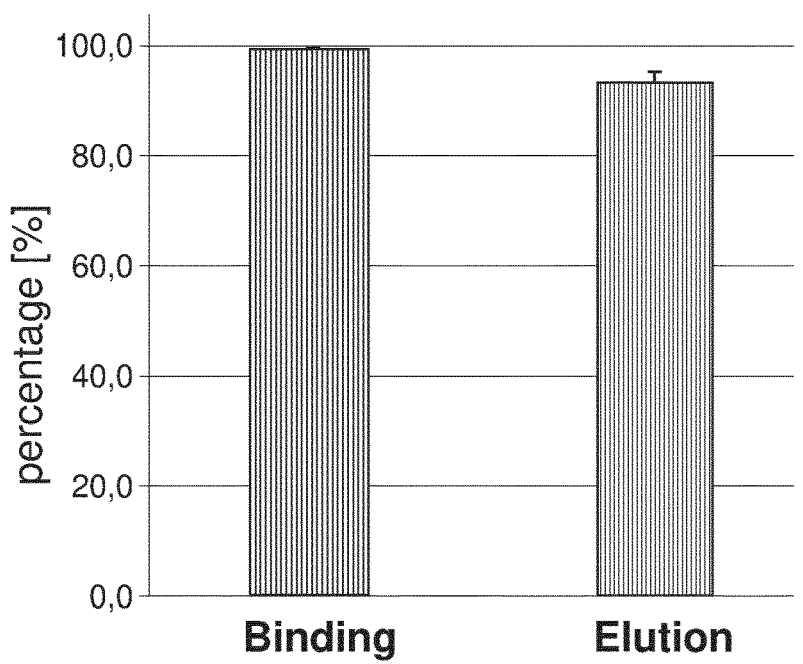

To initiate the culture, the bioreactor was filled with culture medium. This medium contained the components necessary for the cells to grow and produce antibody, such as sugar, amino acids, vitamins, salts, buffer, metal traces, organic components. The cells were inoculated at day 0 from a stock culture maintained in shake flasks. The bioreactor was equipped with a cell retention system Alternative Tangential Flow Filtration with an ultra-filter of 50 kDa cut-off. This allowed performing perfusion operation. With this ultra-filter, the small molecules, which can potentially be toxic for the cells, were removed from the culture while large molecules, in particular the antibody molecules, were retained in the bioreactor. The culture medium was continuously removed from the culture while fresh medium was automatically added so that the culture level was maintained. At day 16, the culture was stopped, the cell density was $103.9 \times 10^6$ cells/ml (see FIG. 3a) and the cell viability, defined as the ratio between the viable cells and the total cell density, was 96.6% (see FIG. 3a). The cells had produced antibodies, which had accumulated in the cell suspension of the bioreactor up to a concentration of 10.8 g/l (see FIG. 3b). The purification was started with the cell suspension of the bioreactor immediately after the termination of the culture by the adsorption of the antibody molecules on the magnetic beads. For this, a volume of 55 ml protein A coupled magnetic beads, which had the property to bind the antibody, was added to 200 ml cell suspension (or cell suspension). The adsorption phase was performed during at least 5 minutes. FIG. 4a shows the adsorption of the antibody in the mixture of the magnetic beads and the cell suspension of the bioreactor. The concentration of the antibody is given as a function of time in minutes, where 0 is the time of addition of the magnetic beads to the cell suspension. The concentration of antibody decreased with time since the antibody molecules, which were adsorbed on the magnetic beads, were not detected anymore in the cell suspension. For this experiment, the adsorption had been performed during two hours to study the kinetics of adsorption of the antibody molecules on the magnetic beads, however one can see that a shorter time than 2 hours is sufficient to capture the antibody on the magnetic beads. For instance, a time of 5 minutes gives already a substantial capture of the antibodies on the beads and after 10 minutes of adsorption, the residual concentration of antibody in the sample was 0.3 g/l. The next step was a washing step with phosphate buffer to remove the cells, cell debris and other impurities. After this, an elution with 55 ml citrate buffer at low pH was performed twice to recover the antibody molecules from the magnetic beads. The low pH elution step is also a step providing virus reduction. FIG. 4b shows the yield of the elution, where it can be seen that more than 90% of the antibody molecules present in the cell suspension of the bioreactor were recovered. From the 1.5 gram antibody present in the 200 ml cell suspension, 1.4 gram antibody were finally recovered in a volume of 110 ml buffer, representing a volume reduction by a factor 1.8. (The cell mass is quite significant at 100 MVC/ml therefore for the calculation of the total mAb 30% of the liquid was accounted as solid fraction. Meaning that 60 ml of the 200 ml was cell mass and did not contain collectable mAb.) Analyzing the purity of the eluted monoclonal antibody regarding the contamination of host cell proteins (HCP), a final HCP concentration in the eluate was found to be 4.8 ppm resulting in a logarithmic reduction factor (LRV) of 2.3. After this the beads can be re-used in multiple new cycles of purification after a washing procedure with citrate buffer, with PBS and with NaOH.

The invention claimed is:

1. A process for the separation of molecules from a suspension comprising cells at a concentration of at least $56 \times 10^6$ cells/ml, comprising the steps of:

growing the cells in a cell medium in a bioreactor, wherein a perfusion method is used, wherein spent cell medium depleted of nutrients and including cell waste products is removed and wherein fresh cell medium is provided to the cells in the bioreactor at the same rate as spent cell medium is removed, wherein molecules with a molecular weight over a determined cut off value are not removed together with the spent cell medium, and wherein the cells in the cell medium form the suspension comprising the cells, which suspension is used in the following steps without any filtration;

providing magnetic particles having a specific interaction with said molecules to be separated;

mixing the magnetic particles with the suspension containing the molecules;

bringing the suspension in contact with a magnetic field provided by a magnetic separation device to collect the magnetic particles;

decreasing or removing said magnetic field and collecting said magnetic particles carrying said molecules; and removing said molecules from said magnetic particles, to provide a concentrated fraction of said molecules, and/or provide partial or complete removal of impurities and cells from the fraction containing the molecules.

2. The process according to claim 1, wherein a bead capacity usage is at least 60%.

3. The process according to claim 1, wherein the magnetic particles and the suspension containing the molecules are in contact no more than 45 minutes after the mixing.

4. The process according to claim 1, wherein the suspension comprising cells has a concentration of at least $70 \times 10^6$ cells/ml.

5. The process according to claim 1, wherein the suspension comprising cells is such that the volume of the cells occupies at least 12% of the culture volume and is any one from the group consisting of cell culture, microorganism fermentation and cell suspension derived from cell tissue.

6. The process according to claim 1, wherein the magnetic particles comprise a component selected from the group consisting of agarose, silica, cellulose, polyvinyl alcohol, polyethylene glycol, polystyrene, acrylate, dextran, and derivatives thereof.

7. The process according to claim 1, wherein the magnetic particles comprise at least one functional group selected from the group consisting of —SH, —SS-pyridine, —COOH, —NH2, —CHO, —OH, phenol, anhydride, epoxy, an S—Au, an amide, an aminoethyl group, a diethylaminoethyl group, a quaternary ammonium group, a carboxymethyl group, a phosphate group, a sulfopropyl group, IDA (iminodiacetic acid) and derivatives thereof, TED (tris (carboxymethyl) ethylenediamine) and derivatives thereof, CM-Asp (carboxymethylated aspartic acid) and its derivatives, NTA (nitrilotriacetic acid) and its derivatives, TREN (tris(2-aminoethyl)amine) and its derivatives, DPA (lutidine) and its derivatives, C6-S gel (hexylthio group) and its derivatives, and EDTA (ethylenediaminetetraacetic acid) and its derivatives.

8. The process according to claim 1, wherein the magnetic particles carry at least one selected from the group consisting of $C_nH_m$ (1≤n≤20, 4≤m≤42), phenol and its derivatives, thiophenol and a group of derivatives of thiophenol, and a group consisting of mercaptopyridine and its derivatives.

9. The process according to claim 1, wherein the magnetic particles comprise at least one functional group comprising at least one group which is produced by reacting with at least one compound selected from the group consisting of divinyl sulfone, benzene anthracene, imidazole, periodate, trichloro-S-triazine, toluenesulfonate, diazo compound, isourea salt, carbodiimide, hydrazine, epichlorohydrin, glutaraldehyde, cyanogen bromide, double Ethylene oxide, carbonyl diimidazole, N-hydroxysuccinimide, silane, and derivatives thereof.

10. The process according to claim 1 wherein the affinity is obtained using molecules suitable for molecular interaction introduced on magnetic particles.

11. The process of claim 10, wherein the molecule suitable for molecular interaction is at least one selected from the group consisting of organic molecules, proteins, antigens, enzymes, enzyme inhibitors, cofactors, hormones, toxins, vitamins, glycoconjugates, nucleic acids, antibodies, peptides, lectins, and carbohydrates.

12. The process according to claim 1, wherein the magnetic particles comprise particles of at least one magnetic material embedded in a polymer matrix, and wherein the polymer matrix comprises functional groups.

13. The process according to claim 1, wherein the suspension containing the molecules comprises at least one selected from the group consisting of alive cells, dead cells, ruptured cells, lysed cells, cell debris, cell membrane, proteins, peptides, DNA, RNA, ions, amino acids, organic compounds, salts, water, solvents and/or metals.

14. The process of claim 13, wherein the cells are eukaryotic cells.

15. The process of claim 14, wherein the eukaryotic cells are selected from the group consisting of mammalian cells, human cells, avian cells, insect cells and plant cells.

16. The process of claim 15, wherein the cells are selected from the group consisting of: CHO, CHO-DBX11, CHO-DG44, CHO-S, CHO-K1, Vero, BHK, HeLa, COS, MDCK, HEK-293, HEK-293T, HEK-293S, HEK-293F, L293, NIH-3T3, W138, BT483, Hs578T, HTB2, BT20, T47D, NSO, CRL7030, HsS78Bst cells, PER.C6, SP2, SPO, hybridoma, MRC-5, MDCK, WI-98, CAP, EB66, AGE1.CR, CR, Trichoplusia ni, Spodoptera Frugiperda, SF9, SF21, Hi5, mesenchymal stem cells, induced pluripotent stem cells, embryonic stem cells, primary cells, Nicotiana tabacum, BY2, Nicotiana benthamiana, Oriza sativa, Arabidopis thaliana, and Daucus carota.

17. The process according to claim 1, wherein the molecules are polypetides, proteins, antibodies, enzymes, viral vectors, viruses, polysaccharides, polymers, exosomes, mRNA, siRNA, or any combination of these, or assemblies derived from these, or assemblies derived from these and associated with a small molecule of a size less than 1000 kDa.

18. The process of claim 1, wherein the cells are selected from the group consisting of Escherichia coli, yeast, Saccharomyces cerevisiae, Pichia pastoris, and Aspergillus niger.

19. The process according to claim 1, wherein the cells are ruptured or lysed by mechanical disruption, ultrasonication, osmotic shock, freeze-thaw, pressure homogenisation, heat treatment or chemical action.

20. The process according to claim 1, wherein the volume of the suspension is at least 100 ml.

21. The process according to claim 1, wherein said magnetic particles are washed at least once before removing said molecules from said magnetic particles.

* * * * *